US00PP32396P2

(12) United States Plant Patent
Hofmann

(10) Patent No.: US PP32,396 P2
(45) Date of Patent: Oct. 27, 2020

(54) ***MANDEVILLA* PLANT NAMED 'INMANBEGRV'**

(50) Latin Name: *Mandevilla sanderi*
Varietal Denomination: Inmanbegrv

(71) Applicant: Birgit Hofmann, Rudesheim am Rhein (DE)

(72) Inventor: Birgit Hofmann, Rudesheim am Rhein (DE)

(73) Assignee: INNOVAPLANT ZIERPFLANZEN GmbH + Co. KG, Gensingen (DE)

( * ) Notice: Subject to any disclaimer, the term of this patent is extended or adjusted under 35 U.S.C. 154(b) by 0 days.

(21) Appl. No.: 16/602,285

(22) Filed: Sep. 6, 2019

(51) Int. Cl.
*A01H 5/02* (2018.01)
*A01H 6/08* (2018.01)

(52) U.S. Cl.
USPC ..... Plt./232
CPC ..... *A01H 6/088* (2018.05)

(58) Field of Classification Search
USPC ..... Plt./232
CPC ..... A01H 6/088
See application file for complete search history.

*Primary Examiner* — Anne Marie Grunberg
(74) *Attorney, Agent, or Firm* — C. A. Whealy

(57) ABSTRACT

A new and distinct cultivar of *Mandevilla* plant named 'Inmanbegrv', characterized by its broadly upright and vining plant habit; moderately vigorous growth habit; freely branching habit; glossy dark green-colored leaves; early and freely flowering habit; large deep velvety red-colored flowers with orange red-colored centers that resist fading; and relative tolerance to low temperatures.

2 Drawing Sheets

Figure 1:
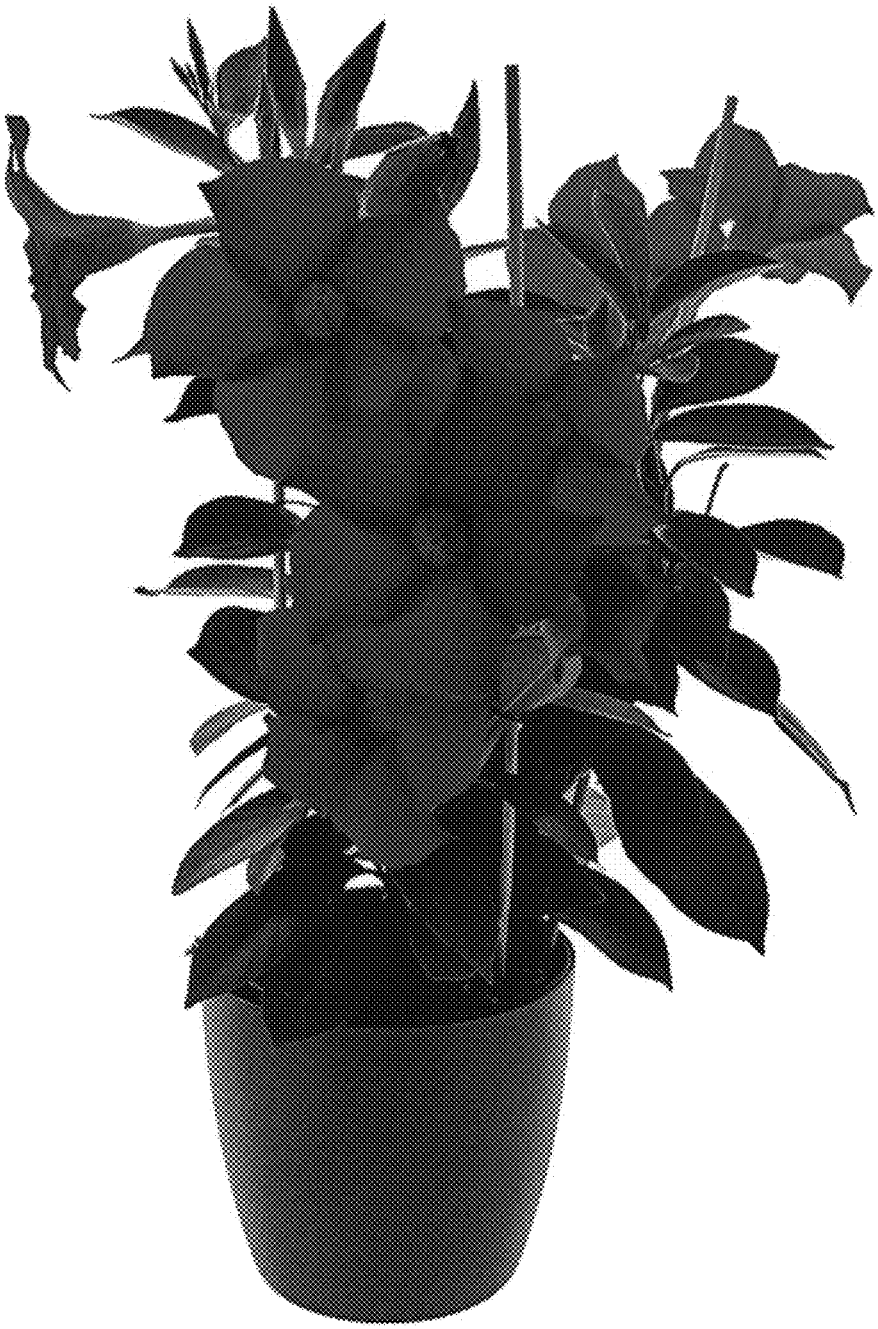

Botanical designation: *Mandevilla sanderi.*
Cultivar denomination: 'INMANBEGRV'.

BACKGROUND OF THE INVENTION

The present invention relates to a new and distinct cultivar of *Mandevilla* plant, botanically known as *Mandevilla sanderi* and hereinafter referred to by the name 'Inmanbegrv'.

The new *Mandevilla* plant is a product of a planned breeding program conducted by the Inventor in Johannesburg, South Africa and Gensingen, Germany. The objective of the breeding program is to create new freely branching *Mandevilla* plants that flower early and freely and have attractive flowers that resist fading and sun scald.

The new *Mandevilla* plant originated from a cross-pollination conducted by the Inventor in Johannesburg, South Africa in January, 2014 of a proprietary selection of *Mandevilla sanderi* identified as code number D11-2140-9, not patented, as the female, or seed parent with a proprietary selection of *Mandevilla sanderi* identified as code number D11-2162-9, not patented, as the male, or pollen, parent. The new *Mandevilla* plant was discovered and selected by the Inventor as a single flowering plant from within the progeny of the stated cross-pollination in a controlled greenhouse environment in Gensingen, Germany in June, 2015.

Asexual reproduction of the new *Mandevilla* plant by vegetative cuttings in a controlled greenhouse environment in Gensingen, Germany since August, 2015 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Inmanbegrv'. These characteristics in combination distinguish 'Inmanbegrv' as a new and distinct *Mandevilla* plant:

1. Broadly upright and vining plant habit.
2. Moderately vigorous growth habit.
3. Freely branching habit.
4. Glossy dark green-colored leaves.
5. Early and freely flowering habit.
6. Large deep velvety red-colored flowers with orange red-colored centers that resist fading.
7. Relatively tolerant to low temperatures.

Plants of the new *Mandevilla* can be compared to plants of the female parent selection. Plants of the new *Mandevilla* differ primarily from plants of the female parent selection in the following characteristics:

1. Plants of the new *Mandevilla* are more upright and have stronger branches than plants of the female parent selection.
2. Plants of the new *Mandevilla* are not as freely branching as plants of the female parent selection.
3. Plants of the new *Mandevilla* have larger leaves than plants of the female parent selection.
4. Plants of the new *Mandevilla* have flatter and more velvety flowers than plants of the female parent selection.

Plants of the new *Mandevilla* can be compared to plants of the male parent selection. Plants of the new *Mandevilla* differ primarily from plants of the male parent selection in the following characteristics:

1. Plants of the new *Mandevilla* are more upright and have stronger branches than plants of the male parent selection.

2. Plants of the new *Mandevilla* are not as freely branching as plants of the male parent selection.
3. Flowers of plants of the new *Mandevilla* are larger and flatter than flowers of plants of the male parent selection.
4. Plants of the new *Mandevilla* have deep velvety red-colored flowers whereas plants of the male parent selection have pink-colored flowers.

Plants of the new *Mandevilla* can also be compared to plants of *Mandevilla hybrida* 'Inmanredeep', disclosed in U.S. Plant Pat. No. 29,096. In side-by-side comparisons, plants of the new *Mandevilla* differ primarily from plants 'Inmanredeep' in the following characteristics:

1. Plants of the new *Mandevilla* are larger and have longer and stronger branches than plants of 'Inmanredeep'.
2. Plants of the new *Mandevilla* are not as freely branching as plants of 'Inmanredeep'.
3. Plants of the new *Mandevilla* have larger flowers than plants of 'Inmanredeep'.
4. Flowers of plants of the new *Mandevilla* are darker red in color than flowers of plants of 'Inmanredeep'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet (FIG. 1 of 2) comprises a side perspective view of a typical flowering plant of 'Inmanbegrv' grown in a container.

Figure 2:
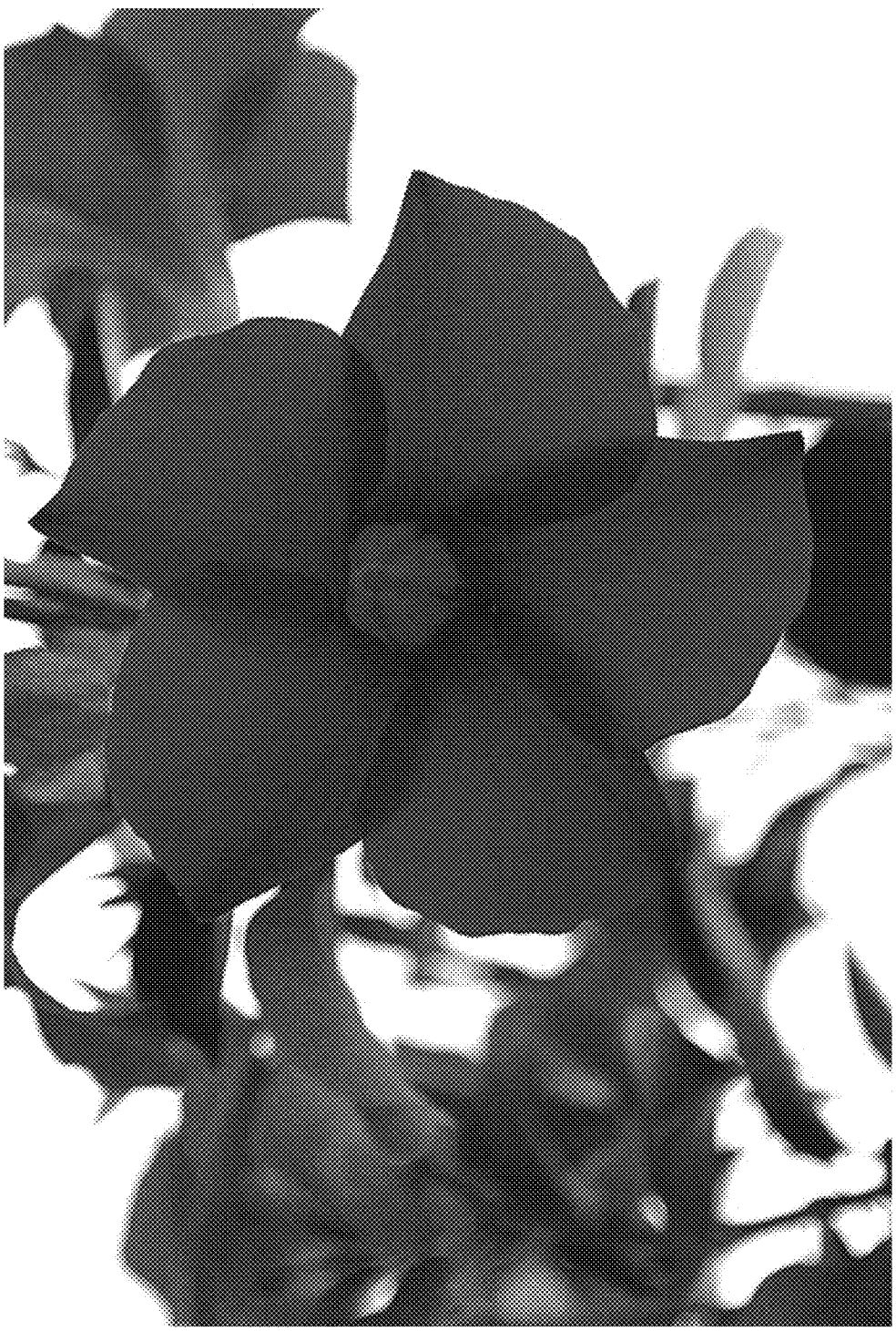

The photograph on the second sheet (FIG. 2 of 2) is a close-up view of a typical flowering plant of 'Inmanbegrv'.

DETAILED BOTANICAL DESCRIPTION

The aforementioned photographs and following observations, measurements and values describe plants grown during the late spring and early summer in 11-cm containers in a glass-covered greenhouse in Heidesheim, Germany and under cultural practices typical of commercial *Mandevilla* production. During the production of the plants, day temperatures ranged from 12° C. to 35° C. and night temperatures ranged from 12° C. to 18° C. Plants were seven months old when the photographs and description were taken. In the following description, color references are made to The Royal Horticultural Society Colour Chart, 2015 Edition, except where general terms of ordinary dictionary significance are used.

Botanical classification: *Mandevilla sanderi* 'Inmanbegrv'.

Parentage:

*Female, or seed, parent*.—Proprietary selection of *Mandevilla sanderi* identified as code number D11-2140-9.

*Male, or pollen, parent*.—Proprietary selection of *Mandevilla sanderi* identified as code number D11-2162-9.

Propagation:

*Type*.—By vegetative cuttings.

*Time to initiate roots, summer*.—About three weeks at temperatures ranging from 20° C. to 35° C.

*Time to initiate roots, winter*.—About three weeks at temperatures ranging from 20° C. to 25° C.

*Time to produce a rooted young plant, summer*.—About 20 to 25 days at temperatures ranging from 20° C. to 35° C.

*Time to produce a rooted young plant, winter*.—About 25 to 30 days at temperatures ranging from 20° C. to 25° C.

*Root description*.—Thick, fleshy; typically white in color, actual color of the roots is dependent on substrate composition, water quality, fertilizers, substrate temperature and physiological age of roots.

*Rooting habit*.—Low branching; medium density.

Plant description:

*Plant and growth habit*.—Broadly upright and vining plant habit; roughly broadly obovate in overall shape; moderately vigorous growth habit and moderate growth rate.

*Plant height, soil level to top of foliar plane*.—About 36.2 cm.

*Plant height, soil level to top of floral plane*.—About 37.5 cm.

*Plant diameter (spread)*.—About 33.9 cm.

*Lateral branch description*.—Branching habit: Freely branching habit, typically about three primary lateral branches each with about two secondary lateral branches. Length: About 21.5 cm. Diameter: About 3 mm. Internode length: About 3.4 cm. Aspect: Primary lateral branches, erect to about 10° from vertical; secondary lateral branches, about 25° from primary branch axis. Strength: Strong. Texture and luster: Smooth, glabrous; glossy; becoming woody with development. Color, developing: Close to 144A. Color, developed: Close to between 143B and 144A; when woody, close to N199A.

Leaf description:

*Arrangement*.—Opposite, simple.

*Length*.—About 7.3 cm.

*Width*.—About 4.2 cm.

*Shape*.—Broadly elliptic to broadly obovate.

*Apex*.—Short apiculate.

*Base*.—Truncate to obtuse.

*Margin*.—Entire; not undulate.

*Texture and luster, upper surface*.—Smooth, glabrous; moderately coriaceous; moderately glossy.

*Texture and luster, lower surface*.—Smooth, glabrous; moderately coriaceous; slightly glossy.

*Venation pattern*.—Pinnate.

*Color*.—Developing leaves, upper surface: Close to 146A; towards the base, close to 152D. Developing leaves, lower surface: Close to 152A to 152B. Full expanded leaves, upper surface: Darker than between 139A and 147A; venation, close to 143B. Fully expanded leaves, lower surface: Close to between 146B and 147B; venation, close to 145B.

*Petioles*.—Length: About 1.1 cm. Diameter: About 2 mm by 2.5 mm. Strength: Moderately strong. Texture and luster, upper and lower surfaces: Smooth, glabrous; slightly glossy. Color, upper surface: Close to 144A. Color, lower surface: Close to 144C.

Flower description:

*Flower type and flowering habit*.—Single salverform flowers arranged in axillary cymes; flowers face outwardly to somewhat upright; freely flowering habit with about six flowers per inflorescence and about 50 flower buds and open flowers developing per plant during the flowering season.

*Natural flowering season*.—Plants flower continuously from spring into the autumn in Germany; plants begin flowering about 16 weeks after propagation (dependent on light level).

*Flower longevity on the plant*.—Individual flowers last about ten days; flowers not persistent.

*Fragrance*.—None detected.

*Inflorescence height*.—About 12.3 cm.

*Inflorescence diameter*.—About 14.3 cm.

*Flower buds*.—Length: About 6.1 cm. Diameter: About 1.2 cm. Shape: Narrowly oblanceolate. Texture and luster: Smooth, glabrous; slightly glossy. Color: Distally, close to between 46A and 185A; towards the base, close to 46A; at the base, close to 145B and 145A.

*Flowers*.—Appearance: Flared trumpet, corolla fused and five-parted. Diameter: Large, about 9.5 cm. Depth (length): About 6.8 cm. Throat diameter: About 1.6 cm. Tube length: About 5.2 cm. Tube diameter: Proximally, about 4 mm; distally, about 1.9 cm.

*Corolla*.—Quantity and arrangement: Five petals arranged in a single whorl; lower 52% portion of the petals are fused into a funnelform tube. Petal length: About 9.8 cm. Petal width: About 3.8 cm. Petal shape and appearance: Roughly unequal spatulate. Petal apex: Apiculate. Petal margin: Entire; slightly undulate. Petal texture and luster, upper surface: Smooth, glabrous; velvety; matte. Petal texture and luster, lower surface: Smooth, glabrous; slightly velvety; slightly glossy. Throat texture: Smooth, glabrous; velvety. Tube texture: Smooth, glabrous; slightly velvety. Color: Petal, when opening, upper surface: More intense than 53A. Petal, when opening, lower surface: Close to 53A. Petal, fully opened, upper surface: Slightly more intense than 53A; venation, similar to lamina; color does not change with development. Petal, fully opened, lower surface: Close to 46A; venation, similar to lamina; color does not change with development. Throat: Close to 31A to 31B; at the base, close to 151B to 151C; venation, similar to lamina. Tube: Close to N45A; proximally, close to 150D and at the base, close to 150A; venation, similar to lamina.

*Calyx*.—Quantity and arrangement: Five sepals arranged in a single whorl. Calyx length: About 8 mm. Calyx diameter: About 5 mm. Sepal length: About 7 mm. Sepal width: About 1.75 mm. Sepal shape: Lanceolate. Sepal apex: Narrowly acuminate. Sepal base: Broadly cuneate. Sepal margin: Entire. Sepal texture and luster, upper and lower surfaces: Smooth, glabrous; moderately glossy. Sepal color: When developing, upper and lower surfaces: Close to 145A; fading towards the base to close to 143B; at the apex, close to 179B. Fully developed, upper and lower surfaces: Close to 144C; at the apex, close to 179B.

*Peduncles*.—Length: About 9 cm. Diameter: About 2 mm. Strength: Strong. Aspect: About 30° from lateral branch axis. Texture and luster: Smooth, glabrous; glossy. Color: Close to 144A.

*Pedicels*.—Length: About 2.1 cm. Diameter: About 2 mm. Strength: Strong. Aspect: About 15° to 40° from peduncle axis. Texture and luster: Smooth, glabrous; moderately glossy. Color: Close to 143C.

*Reproductive organs*.—Stamens: Quantity and arrangement: Typically five; basifixed; anthers connivent. Filament length: About 3 mm. Filament color: Close to 153D. Anther shape: Narrowly oblong. Anther size: About 9 mm by 1.5 mm. Anther color: Close to 161D. Pollen amount: None observed. Pistils: Quantity: Typically one. Pistil length: About 2.2 cm. Style length: About 1.9 cm. Style color: Close to 145D. Stigma diameter: About 2 mm. Stigma shape: Club-shaped, pointed. Stigma color: Close to 153D. Ovary color: Close to 143C.

*Seeds and fruits*.—To date, seed and fruit production have not been observed on plants of the new *Mandevilla*.

Pathogen & pest resistance: To date, plants of the new *Mandevilla* have not been noted to be resistant to pathogens and pests common to *Mandevilla* plants.

Temperature tolerance: Plants of the new *Mandevilla* have been observed to tolerate temperatures ranging from about 5° C. to about 40° C. and to be suitable for USDA Hardiness Zones 9 to 13.

It is claimed:

1. A new and distinct *Mandevilla* plant named 'Inmanbegrv' as illustrated and described.

* * * * *